United States Patent
Holderich et al.

Patent Number: 5,780,687
Date of Patent: Jul. 14, 1998

[54] PROCESS FOR PREPARING 3-OXYALKYLPROPAN-1-OLS

[75] Inventors: Wolfgang Holderich, Frankenthal; Marcus Paczkowski, Darmstadt; Dieter Heinz, Meerbusch; Thomas Kaiser, Kelkeim, all of Germany

[73] Assignee: Hoechst Aktiengesellschaft, Germany

[21] Appl. No.: 863,258

[22] Filed: May 27, 1997

[30] Foreign Application Priority Data

May 30, 1996 [DE] Germany .................. 196 21 703.2

[51] Int. Cl.⁶ .................................................. C07C 41/03
[52] U.S. Cl. ...................... 568/678; 568/662; 568/670
[58] Field of Search ............................ 568/678, 662, 568/670

[56] References Cited

FOREIGN PATENT DOCUMENTS

| 0133881 | 3/1985 | European Pat. Off. |
| 0092463 | 10/1983 | France. |
| 1234199 | 9/1964 | Germany. |
| 2819159 | 11/1979 | Germany. |
| 3224033 | 1/1983 | Germany. |

OTHER PUBLICATIONS

Journal of Chemical Society, Chemical Comm., 1981, 3 pgs. Bartok et al.

*Primary Examiner*—Deborah C. Lambkin
*Assistant Examiner*—Ebenezer O. Sackey
*Attorney, Agent, or Firm*—Bierman, Muserlian and Lucas

[57] ABSTRACT

A process for preparing 3-oxyalkylpropan-1-ols by catalytic hydrogenation of 1,3-dioxanes with catalysts comprising a hydrogenation-active component on an acid support.

20 Claims, No Drawings

5,780,687

PROCESS FOR PREPARING 3-OXYALKYLPROPAN-1-OLS

FIELD OF THE INVENTION

A new process for preparing 3-oxyalkylpropan-1-ols starting from readily obtainable 1,3-dioxanes which are hydrogenated in the presence of catalysts containing a hydrogenation-active component and an acid support.

STATE OF THE ART 3-oxyalkylpropany-1-ols are used as solvents and they are also important as building blocks for the synthesis of esters which are used as plasticizers for plastics, particularly for polyvinyl chloride. These esters have a high compatibility with the polymer, are physiologically acceptable and have a low volatility. Furthermore, 3-oxyalkylpropan-1-ols are used as intermediates for the synthesis of biologically active compounds.

It is known that aliphatic monoethers of 2,2-dimethylpropane-1,3-diol having alkoxy groups of 3 to 20 carbon atoms can be prepared from cyclic acetals of 2,2-dimethylpropane-1,3-diol with straight-chain or branched, saturated or unsaturated aliphatic aldehydes of 3 to 20 carbon atoms(i.e. 5,5-dimethyl-2-alkyl-1,3-dioxanes) by hydrogenation in the presence of copper chromite or nickel oxide catalysts (DE 33 28 561 A1). Copper chromite and nickel oxide can here also be used, if desired, on inert supports.

The use of copper chromite catalysts is undesirable for reasons of occupational hygiene since they are prepared from highly toxic chromates. There are also misgivings about the use of nickel catalysts because nickel is toxic and carcinogenic. In addition, out of economic considerations, catalysts having as low as possible a content of hydrogenation-active metal are preferred. However, the low metal concentration should not be at the expense of catalyst effectiveness and selectivity.

OBJECTS OF THE INVENTION

It is an object of the invention to provide a process which avoids the disadvantages indicated, is industrially simple to carry out and can be applied generally.

It is another object of the invention to provide a selective process to ensure high yields of the target products and to be able to be carried out both in the gas phase and in the liquid phase.

These and other objects and advantages of the invention will become obvious from the following detailed description.

THE INVENTION

The novel process of the invention for preparing 3-oxyalkyl-propan-1-oles of the formula

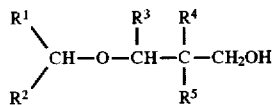

comprises hydrogenating 1,3-dioxanes of the formula

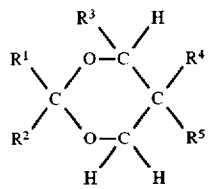

wherein $R^1$, $R^2$, $R^4$ and $R^5$ are individually selected from the group consisting of a) hydrogen, b) straight-chain or branched alkyl, alkenyl and alkynyl of up to 18 carbon atoms, c) cycloalkyl and cycloalkenyl of 5 to 8 carbon atoms, d) aryl, alkylaryl, aralkyl, aralkenyl and alkenylaryl of 6 to 16 carbon atoms and e) heterocyclics or $R^1$ and $R^2$ and/or $R^4$ and $R^5$ together with the carbon atom to which they are attached form a cycloalkane, cycloalkene or heterocycle of 5 to 7 ring atoms, $R^1$, $R^2$, $R^4$ and $R^5$ optionally substituted with an inert member under the reaction conditions, and $R^3$ is hydrogen or alkyl, at pressures of from 0.1 to 35 MPa and temperatures of from 40° to 500° C. in the presence of catalysts, wherein the catalysts comprise at least one metal selected from the group consisting of groups VIB, VIIIB and IB of the Periodic Table of the Elements, with the exception of chromium and nickel, as hydrogenation-active component and an acid support.

Preferred 1,3-dioxanes of formula II are compounds in which $R^1$, $R^2$, $R^4$ and $R^5$ are individually a) hydrogen, b) straight-chain or branched alkyl radicals of 1 to 12 and preferably 1 to 6 carbon atoms, alkenyl or alkynyl of 2 to 12 and preferably 2 to 6 carbon atoms. Also preferred are compounds of formula II in which $R^1$, $R^2$, $R^4$ and $R^5$ are cycloalkyl and cycloalkenyl of 5 to 6 carbon atoms, aryl, alkylaryl, aralkyl, aralkenyl and alkenylaryl of 6 to 12 carbon atoms and heterocyclics containing at least one ring member selected from the group consisting of nitrogen, oxygen and sulfur. Furthermore, preference is given to 1,3-dioxanes of formula II wherein $R^3$ is a straight-chain or branched alkyl of 1 to 12, preferably 1 to 8 and more preferably 1 to 4, carbon atoms. $R^3$ is preferably hydrogen.

Examples of alkyl, alkenyl or alkynyl are methyl, ethyl, n-propyl, i-propyl, propenyl, i-propenyl, n-butyl, i-butyl, n-butenyl, i-butenyl, n-butynyl, pentyl, pentenyl, pentynyl, hexyl, hexenyl, heptyl, heptenyl, octyl, octenyl, nonyl, nonenyl, decyl, decenyl, dodecyl and dodecenyl.

Examples of cycloalkyl are cyclopentyl, cyclohexyl, cycloheptyl, cyclopentenyl and cyclohexenyl.

Examples of aromatics are phenyl, benzyl, 2-phenylethyl, 2-phenylpropyl, 3-phenylpropyl, 2-phenylbutyl, 3-phenylbutyl and 4-phenylbutyl.

Examples of heterocyclics are furan, dihydrofuran, tetrahydrofuran, thiophene, dihydrothiophene, pyridine and thiopyran.

The alkyl, cycloalkyl, aromatic and heterocyclic radicals may be substituted, particularly by groups which are inert under the reaction conditions, for example halogen, alkoxy, carboxy or carboxylate. However, in individual cases, the deliberate selection of substituents which are changed during the course of the reaction, e.g. carbonyls which are converted into hydroxymethyls, is not ruled out.

The 1,3-dioxanes used as starting material in the process of the invention are obtainable in various known ways. A proven method is the acid-catalyzed addition of 1,3-diols onto aldehydes or ketones or the transacetalation of acetals or ketals, particularly those which are derived from low-boiling alcohols, with 1,3-diols in the presence of acids.

Examples of diol components are 1,3-propanediol, 2-methylpropane-1,3-diol, 2-ethylpropane-1,3-diol, 2-phenylpropane-1,3-diol, 2,2-dimethylpropane-1,3-diol (neopentyl glycol), 2,2-diethylpropane-1,3-diol, 2-methyl-2-ethylpropane-1,3-diol, 2-methyl-2-propylpropane-1,3-diol,2-methyl-2-butylpropane-1,3-diol, 2-methyl-2-phenylpropane-1,3-diol, 2-ethyl-2-butylpropane-1,3-diol, 1,1-dimethylolcyclohexane, 1,1-dimethylolcyclopentane, 3,3-dimethyloltetrahydrofuran, 3,3-dimethyloltetrahydropyran and 2,2,4-trimethylpentane-1,3-diol.

Carbonyl compounds reacted with the 1,3-diols are, for example, aliphatic, aromatic or heterocyclic aldehydes and ketones or their acetals or ketals. Both the aldehydes and the ketones can be saturated or unsaturated.

Examples of suitable aliphatic aldehydes are formaldehyde, acetaldehyde, propionaldehyde, butyraldehyde, isobutyraldehyde, n-pentanal, 2-methylbutanal, 3-methylbutanal, n-hexanal, 2-methylpentanal, 3,3-dimethylbutanal, 2-ethylhexanal, 2-methyldecanal, also dialdehydes such as glyoxal, methylglyoxal, malonic dialdehyde, succinic dialdehyde and glutaric dialdehyde, and substituted aldehydes such as 3-hydroxy-2,2-dimethylpropanol (hydropivalaldehyde), methoxypivalaldehyde, butoxypivalaldehyde, 4-acetoxybutyraldehyde and 5-formylvaleraldehyde.

Unsaturated aliphatic aldehydes can also be used as reaction components for the 1,3-diols, e.g. acrolein, α-methylacrolein, α-ethylacrolein and higher α-alkylacroleins, isoalkylacroleins and alkenylacroleins such as but-2-enal, 2-methylbut-2-enal, 2-methylpent-2-enal, 2-ethylhex-2-enal, 2,2-dimethylpent-4-enal, 2-methyl-4-acetoxybut-2-enal, 2-methoxymethylacrolein, 2-(3-methoxycarbonylpropyl)acrolein and 2-methyl-4-chlorobut-2-enal.

Aromatic aldehydes which may be mentioned by way of example are benzaldehyde, p-methoxybenzaldehyde, phenylacetaldehyde, 2-phenylpropanal, 3-phenylpropanal, 2-hydroxybenzaldehyde, 3-hydroxy-4-methoxybenzaldehyde, cinnamaldehyde and benzylacrolein.

Examples of heterocyclic aldehydes are tetrahydrofuryl-2-aldehyde, tetrahydrofuryl-3-aldehyde, tetrahydrothienyl-2-aldehyde, tetrahydrothienyl-3-aldehyde, 5,6-dihydropyranyl-6-aldehyde, 2,5-dimethyl-5,6-dihydropyranyl-6-aldehyde, furyl-2-aldehyde, furyl-3-aldehyde, thienyl-3-aldehyde and 2-, 3- or 4-pyridylaldehyde.

Ketones suitable for preparing the 1,3-dioxanes are, for example, acetone, methyl ethyl ketone, diethyl ketone, methyl isopropyl ketone, diisopropyl ketone, diisobutyl ketone, methyl isobutyl ketone, methoxyacetone, methyl phenyl ketone, methyl isopropenyl ketone, methyl isobutenyl ketone, cyclopentanone, cyclohexanone, dimethylcyclopentanone, dimethylcyclohexanone, cyclohexenone, 3,5,5-trimethylcyclohexen-2-one, ethyl phenyl ketone and vinyl phenyl ketone, methyl furyl ketone, acetylacetone and acetoacetic esters.

The abovementioned diols, aldehydes and ketones as building blocks for the 1,3-dioxanes used in the invention are intended only to indicate roughly the range of application of the new process, but do not restrict it to these compounds mentioned by way of example.

Other reactions which lead to 1,3-dioxanes are the reaction of Grignard reagents with ortho esters and the reaction of alkoxides of diols either with geminal halides or with α-haloethers. Finally, 1,3-dioxanes can also be obtained by the Prins reaction, i.e. the addition of an olef in onto formaldehyde in the presence of an acid.

The hydrogenation of the 1,3-dioxanes in the process of the invention is carried out at from 40° to 500° C. Preference is given to temperatures of 100° to 450° C. and particularly 150° to 350° C. The reaction pressure can be varied over a wide range and is 0.1 to 35 MPa, with pressures of 3 to 15 MPa being preferred.

The molar ratio of hydrogen to 1,3-dioxanes is 0.2:1 to 250:1 and preferably 1:1 to 100:1.

The reactants are reacted in the presence of hydrogenation catalysts. These catalysts comprise as hydrogenation-active components, a metal or a plurality of metals of groups VIB, VIIIB and IB of the Periodic Table of the Elements (in accordance with the naming of groups used by Chemical Abstracts, which will also be used below), with the exception of chromium and nickel. Preferred hydrogenation-active components are molybdenum, tungsten, ruthenium, cobalt, rhodium, iridium, palladium, platinum and, in particular, copper.

Apart from the specific hydrogenation-active metals, the selection of the supports is important for the catalysts employed in the invention. For this purpose, acid compounds are used individually or in the form of mixtures of different acid substances.

Among the many acid compounds, particularly suitable compounds are zeolites which term refers to crystalline, hydrated aluminosilicates having a framework structure and containing alkali metal and/or alkaline earth metal cations. They occur naturally and are also produced synthetically. Zeolites have a structure in which there is a regular system of intercrystalline voids which is accessible, via pore openings, to molecules of similar size.

The framework of the zeolites is made up of tetrahedra, with four oxygen atoms surrounding the central atom, which can be either an $Si^{4+}$ or $Al^{3+}$ cation. Each alumimun atom built into the structure leads to a negative charge in the framework, which is balanced by cations such as alkali metal or alkaline earth metal ions. An exchange of the cations is possible: zeolites are inorganic ion exchangers. Thus, for example, alkali metal ions can be replaced by hydrogen ions. In this way, the catalytic activity of the zeolites, which is dependent on the presence of acid centers in the intercrystalline surface, can be varied. The spaces between the tetrahedra are occupied by water molecules and dehydration by drying or calcination is possible.

In the crystal lattice of synthetically produced zeolites, aluminum can be isomorphically replaced by other elements such as boron, gallium, iron, chromium, vanadium, arsenic and antimony. Silicon can be isomorphically replaced by tetravalent elements such as germanium, titanium, zirconium and hafnium.

The type and extent of the replacement of aluminum and/or silicon allow the catalytic properties of the zeolites to be influenced in a targeted manner and matched to individual requirements.

The zeolites are classified into various groups on the basis of their structure. In the zeolites of the mordenite group, the basic units of the structure, viz. the $SiO_4$ and $AlO_4$ tetrahedra, form chains. The zeolites of the chabasite group are made up of layers of tetrahedra. In the zeolites of the faujasite group, the tetrahedra are arranged to form polyhedra, e.g. in the form of a cuboctahedron. Depending on the linking of the cuboctahedra, voids and pores of different sizes are formed. Differentiation is accordingly made between, for example, zeolites of type A, L, X or Y.

As support component for the catalysts used in the process of the invention, suitable zeolites are those from the faujasite group, e.g. the zeolite Y, zeolites from the mordenite group or narrow-pore zeolites, e.g. of the erionite or chabasite type. Preference is given to using zeolites of the pentasil type which have as basic building block a five-membered ring built of $SiO_4$ tetrahedra and have a high $SiO_2/Al_2O_3$ ratio. Their pore sizes are between those of the zeolites of type A (pore openings 4.1 Å) and those of type X or Y (pore openings 7.4 Å).

The pentasil zeolites can have different chemical compositions. Accordingly, differentiation is made between aluminosilicate, borosilicate, iron silicate, gallium silicate, chromium silicate, arsenic silicate, antimony silicate and bismuth silicate zeolites or their mixtures, and also aluminogermanate, borogermanate, galliumgermanate and iron germanate zeolites or their mixtures.

As supports for the catalysts used in the process of the invention, preference is given to using aluminosilicate, borosilicate and iron silicate zeolites of the pentasil type. The aluminosilicate zeolite is prepared, for example, from an aluminum compound, preferably $Al(OH)_3$ or $Al_2(SO_4)_3$, and a silicon component, preferably finely divided silicon dioxide in aqueous amine solution, particularly in a solution of 1,6-hexanediamine, 1,3-propanediamine or triethylenetetramine, with or without addition of alkali metal or alkaline earth metal hydroxide, at 100° to 220° C. under autogenous pressure. Such a process is described in EP 0 007 081 and EP 0 007 098. These also include the isotactic zeolites as described in EP 0 034 727 and EP 0 046 504. Depending on the amounts of starting material selected, the $SiO_2/Al_2O_3$ ratio in the aluminasilicate zeolites synthesized is 10–40,000:1 (in mol). According to another method, aluminosilicate zeolites are obtained by reacting aluminum and silicon components in an ether such as diethylene glycol dimethyl ether, in an alcohol such as methanol or 1,4-butanediol or in water.

Borosilicate zeolites can be synthesized from a boron compound, e.g. $H_3BO_3$, and a silicon compound, preferably finely divided silicon dioxide, in an aqueous solution of an amine, particularly 1,6-hexanediamine, 1,3-propanediamine or triethylenetetramine, with or without addition of alkali metal or alkaline earth metal hydroxide, at 90° to 200° C. under autogenous pressure. Instead of carrying out the reaction in aqueous amine solution, it can also be carried out in an ether, e.g. in diethylene glycol dimethyl ether, or in an alcohol, e.g. in 1,6-hexanediol, as solvent (cf. EP 0 007 081 and EP 0 007 098).

The iron silicate zeolites are obtained, for example, starting from an iron compound, preferably $Fe_2(SO_4)_3$, and a silicon compound, preferably finely divided silicon dioxide, which are reacted in an aqueous solution of an amine, particularly 1,6-hexanediamine, with or without addition of alkali metal or alkaline earth metal hydroxide, at 100° to 200° C. under autogenous pressure (cf. EP 0 007 081 and EP 0 007 098).

The aluminosilicate, borosilicate or iron siliciate zeolites are, after their preparation and isolation, dried at 100° to 160° C., preferably 110° to 130° C., and then calcined at 450° to 550°, preferably 480° to 520° C. Subsequently, they are shaped with addition of a binder, for example to form extrudates or pellets. Suitable binders are the various aluminum oxides, preferably boehmite, amorphous aluminosilicates having an $SiO_2/Al_2O_3$ weight ratio of 0.3:1 to 18:1, preferably 3:1 to 5:1, silicon dioxide, particularly finely divided $SiO_2$, mixtures of finely divided $SiO_2$ and finely divided $Al_2O_3$, finely divided $TiO_2$ and also clay. Binder and zeolite are used in a weight ratio of 90:10 to 40:60. After shaping, the shaped bodies are again dried for 10 to 20 hours at 110° to 130° C. and calcined at 400° to 550° C. for a time between 10 and 20 hours.

Instead of being calcined immediately after preparation, isolation and drying, the zeolites can also be dried and shaped and subsequently calcined. Finally, it is also possible to omit the use of binders and to carry out the shaping procedure using shaping or peptizing aids such as ethylcellulose, stearic acid, potato starch, formic acid, oxalic acid, acetic acid, nitric acid, ammonia, amines, silicoesters or graphite or mixtures thereof.

Zeolites which, because of the way in which they are prepared, contain alkali metal or alkaline earth metal ions but no or not enough $H^+$ ions have to be converted into the acid, catalytically active H form by ion exchange. For this purpose, they are treated with acids or ammonium ions are introduced and they are subsequently calcined. The acidity required for the specific application can be set by means of partial ion exchange.

Furthermore, the zeolites can be modified by ion exchange or by impregnation with certain metals, for example to improve the selectivity of the reaction or to increase the catalyst life. Doping of the zeolites may be with transition metals of groups VIB, VIIIB, IB and IIB, with the exception of chromium and nickel, for example molybdenum, tungsten, iron, copper and zinc, with noble metals such as palladium and platinum and with metals of the rare earths, for example lanthanum, cerium and praseodymium.

For the doping by ion exchange, the shaped or unshaped zeolite is treated, for example, at temperatures of 20° to 100° C. with an aqueous or ammoniacal solution of a salt, for example a halide, nitrate or acetate, of the above described metals. The ion exchange can be carried out using zeolites in the hydrogen, ammonium or alkali metal form.

For example, extrudates or pellets of the zeolite in the H form are placed in a column and an ammoniacal $Pd(NO_3)_2$ solution is circulated over the shaped base at temperatures of 30° to 80° C. for 15 to 20 hours. The zeolite is subsequently washed with water, dried at about 150° C. and calcined at about 550° C.

According to another variant of the ion exchange process, the pulverulent zeolite is suspended in a metal salt solution, e.g. in an ammoniacal $Pd(NO_3)_2$ solution, and is stirred at 40° to 100° C. for about 24 hours. After filtering off, drying at about 150° C. and calcining at about 500° C., the modified zeolite can be further processed with or without binder to give extrudates, pellets or fluidizable material.

The doping of the zeolites by impregnation can also be carried out using metal salts, e.g. chlorides, nitrates or acetates, in aqueous, ammoniacal or alcoholic solution. One possible embodiment comprises largely dissolving tungstic acid, $H_2WO_4$, for example, in water and impregnating the shaped or unshaped zeolite with this solution for a certain period of time, e.g. 30 minutes. The water is then removed from the supernatant solution by evaporation, the zeolite is dried at about 150° C. and calcined at about 550° C. This impregnation procedure can be repeated a number of times until the desired metal content is obtained.

The doping of the zeolites with metals, regardless of whether it has been carried out by ion exchange or by impregnation, can be followed by an after-treatment with hydrogen.

A further way of modifying the zeolites can comprise a treatment with inorganic or organic acids such as hydrochloric acid, hydrofluoric acid or phosphoric acid and/or with water vapor.

Phosphates have also been found to be suitable as supports for catalysts which are used in the process of the invention. Particularly suitable phosphates are aluminum phosphates, cerium phosphates, zirconium phosphates, boron phosphates, iron phosphates, strontium phosphates, silicon aluminum phosphates, silicon iron aluminum phosphates or mixtures thereof.

Supports based on aluminum phosphates for the catalysts employed in the process are advantageously obtained by synthesis under hydrothermal conditions. These aluminum phosphates include, for example, APO-5, APO-9, APO-11, APO-12, APO-14, APO-21, APO-25, APO-31 and APO-33. These aluminum phosphates have a zeolite structure (on this subject, see Flanigen, et al., Structural Synthetic and Physicochemical Concepts in Aluminophosphate-based Molecular Sieves, Innovation in Zeolite Materials Science |Editors: P. J. Grobet et al.| Elsevier, 1988, p. 13 ff).

$AlPO_4$-5 (APO-5) is obtained, for example, by reacting a homogeneous mixture of orthophosphoric acid and pseudoboehmite in water, admixed with tetrapropylammonium hydroxide, in an autoclave at about 150° C. for a reaction time of 20 to 60 hours under autogenous pressure. The $ALPO_4$ filtered off is dried at 100 to 160° C. and calcined at 450 to 550° C.

$AlPO_4$-9 (APO-9) is synthesized from orthophosphoric acid and pseudoboehmite in an aqueous 1,4-diazabicyclo |2.2.2|-octane solution at about 200° C. under autogenous pressure, with the reaction time of 200 to 400 hours.

The synthesis of $AlPO_4$-21 (APO-21) is carried out by reacting orthophosphoric acid and pseudoboehmite in an aqueous pyrrolidine solution at 150° to 200° C. for a reaction time of 50 to 200 hours under autogenous pressure.

Aluminum phosphates suitable as supports can also be obtained by precipitation. They are obtained, for example, by adding a solution of 268 g of $Al(NO_3)_3.H_2O$ in 780 ml of water dropwise to a solution of 92 g of diammonium hydrogen phosphate in 700 ml of water over a period of 2 hours. A pH of 8 is maintained by simultaneous addition of 25% strength $NH_3$ solution. The resulting precipitate is stirred further for 12 hours, vacuum filtered, washed and dried for 16 hours at 60° C.

Examples of silicon aluminum phosphates as supports for the catalysts used in the invention are SAPO-5, SAPO-11, SAPO-31 and SAPO-34. These silicon aluminum phosphates also have a zeolite structure (on this sunject, see Szostak et al., Catalysis Letters, Vol. 12 (1989), p. 63 ff). They are obtained by reacting a mixture of silicon, aluminum and phosphorus components in aqueous, organic amine solutions at 100° to 250° C. for a reaction time of 2 hours to 2 weeks under autogenous pressure. SAPO-5 is obtained, for example, by mixing a suspension of $SiO_2$ in an aqueous tetrapropylammonium hydroxide solution with a suspension of pseudoboehmite and orthophosphoric acid in water and subsequently reacting the resulting mixture at 150° to 200° C. for a reaction time of 20 to 200 hours in a stirring autoclave under autogenous pressure. The powder filtered off is dried at 110° to 170° C. and calcined at 450° to 550° C.

Other suitable silicon aluminum phosphates include, for example, ZYT-5, ZYT-6, ZYT-7, ZYT-9, ZYT-11 and ZYT-12.

Boron phosphates which can serve as supports for the catalysts used in the process are obtained, for example, by mixing and kneading concentrated boric acid and phosphoric acid, drying the mixture and calcining it in an atmosphere of inert gas, air or steam at 250° to 650° C., preferably 300° to 500° C.

The supports based on phosphates too can be modified to increase the selectivity, the yield and the catalyst life. One way of doing this is doping the unshaped or shaped phosphates with metal salts by ion exchange or impregnation. The doping is carried out using transition metals of groups IVB to VIIIB of the Periodic Table, with the exception of chromium and nickel, for example titanium, zirconium, vanadium, niobium, molybdenum, tungsten, manganese, rhenium, iron, ruthenium osmium, cobalt, rhodium, iridium, palladium and platinum, transition metals of groups IB and IIB of the Periodic Table, for example copper, silver and zinc, also tin, the metals of the rare earths, for example lanthanum, cerium, praseodymium, neodymium, erbium and ytterbium, and also uranium. Alkali metals such as lithium, potassium and cesium, alkaline earth metals such as magnesium, calcium and strontium, metals of groups IIIA, IVA and VA of the Periodic Table, for example aluminum, gallium, germanium, tin, lead and bismuth can already be present in the support material as additional promoters or be introduced. Like the zeolites, the phosphates too can be modified by treatment with inorganic or organic acids.

Finally, other supports which can be used for catalysts for hydrogenating 1,3-dioxanes are metal oxides having acid or amphoteric properties. Suitable metal oxides are, for example, the acidic oxides of metals of groups IIIA and IVA and groups IVB to VIB of the Periodic Table, with the exception of chromium, in particular silicon dioxide in the form of silica gel and kieselguhr, also titanium oxide, zirconium dioxide, the phosphorus oxides, vanadium pentoxide, niobium oxides, boron trioxide, aluminum oxide, molybdenum oxides, tungsten oxides and also iron oxides, either alone or as a mixture of two or more of these compounds.

It has been found to be advantageous to treat the oxides mentioned with inorganic or organic acids. Suitable inorganic acids are, for example, HF, HCl, HBr, HI, $H_2SO_4$, $H_2SO_3$, $HNO_3$, $H_3BO_3$, the phosphorous acids and their mixtures. Organic acids which are suitable for treatment of the oxides are, for example, formic acid, acetic acid, propionic acid and oxalic acid, either alone or in admixture. Mixtures of inorganic and organic acids can also be used. The acids are allowed to act on the shaped or unshaped material.

$SiO_2$ (silica) in powder form is, for example, treated for 1 hour at 80° C. with 1N acid. It is then washed with water, dried for 16 hours at 110° C. and calcined for 20 hours at 500° C. Another method is to treat $SiO_2$, before or after shaping, for 1 to 3 hours at from 60° to 80° C. with 3–25% strength by weight, particularly 12–20% strength by weight, aqueous hydrochloric acid, subsequently wash the $SiO_2$ with water, dry it and calcine it at 400° to 500° C.

According to a particularly advantageous embodiment, $SiO_2$ is treated prior to shaping by heating with 0.001–2N, preferably 0.05–0.5N, hydrofluoric acid, for example, under reflux generally for a time of 0.5 to 5 hours, preferably 1 to 3 hours. The support material is isolated, washed, advantageously dried at temperatures of 100° to 160° C. and calcined at 450° to 600° C. According to another preferred embodiment of the acid treatment, 12–20% strength by weight hydrochloric acid is allowed to act at elevated temperature, e.g. 50° to 90° C., preferably 60° to 80° C., on $SiO_2$ after shaping for 0.5 to 5 hours, preferably 1 to 3 hours. The material is subsequently washed, dried at 100° to 160° C. and calcined at 450° to 600° C. The treatment with hydrofluoric acid can also be followed by treatment with hydrochloric acid.

Phosphoric acid is applied to the metal oxide support material, e.g. $SiO_2$, $Al_2O_3$ or $TiO_2$, by impregnation or spraying. Thus, a support containing phosphoric acid is obtained, for example, by treating $SiO_2$ with a $H_3PO_4$ or $NaH_2PO_4$ solution and subsequently drying or calcining it. Phosphoric acid can also be sprayed together with silica gel in a spray tower. This process is followed by drying and usually calcination. Finally, phosphoric acid can be sprayed onto silicon dioxide in an impregnation mill.

The above-described support materials of the zeolite, phosphate and metal oxide type are the basis for the catalysts used in the process of the invention. For this purpose, the supports have to be loaded with the hydrogenation-active component or components. As already mentioned, the hydrogenation-active components are metals of groups VIB, VIIIB, IB and IIB of the Periodic Table of the Elements, with the exception of chromium and nickel.

The support and hydrogenation-active metal can be combined in various ways. If the supports are capable of ion exchange, they are treated with solutions of the hydrogenation-active metals and the exchangeable cations in the crystal structure are replaced by the ions of the catalytically active metals. It is advantageous to use metal compounds whose anions are thermally unstable and can be removed by heating, for example acetate, nitrate, carbonate and oxalate. The extent of the ion exchange is determined by the ion exchange isotherms. The loading of the supports with the active metal can also be combined with the doping as described above by carrying out the ion exchange using solutions containing ions of both the hydrogenation-active metal and the doping metal.

In practice, the ion exchange is carried out by stirring pulverulent molecular sieves with an ammoniacal metal salt solution at 20° to 80° C. for 1 to 48 hours, preferably 6 to 36 hours. The metal concentration on the support is calculated from the difference in the metal ion concentrations before and after ion exchange. The powder loaded with the metal is washed with distilled water, dried at 110° to 160° C. and calcined at 400° to 650° C. using a heating rate of 0.1 to 10° C. min$^{-1}$.

Another method of applying the hydrogenation-active component comprises impregnating the catalyst support with the metal salt solution. In practice, the catalyst support, for example, is stirred with an ammoniacal solution of the metal salt at 20° to 80° C. for 1 to 48 hours, preferably 6 to 36 hours. The solvent is distilled off, the loaded support is dried at 110° to 160° C. and calcined at 400° to 650° C. In the case of the impregnation process too, application of the hydrogenation-active components and doping of the support can be carried out in one step.

A further method of preparing hydrogenation catalysts which are suitable for the new process is joint precipitation of hydrogenation and support components. Two possibilities can be distinguished here. Either the hydrogenation-active component is precipitated onto the previously made support or the hydrogenation-active component and support are precipitated jointly. In practice, for example, the metal salt solution in which the support material is suspended, is initially charged and the metal is precipitated as a sparingly soluble compound, for example as hydroxide, bicarbonate, carbonate or basic carbonate, onto the support using a basic reagent. In the simultaneous precipitation of hydrogenation-active and support components, a combined solution of the starting compounds is reacted with the precipitant. The precipitate is stirred further, if appropriate, at room temperature or elevated temperature, filtered, washed, dried and calcined.

Depending on the method employed, the support material is loaded with different amounts of the hydrogenation-active components. When catalysts are obtained by ion exchange, the maximum metal concentration is limited by the exchange capacity of the support material. Such catalysts usually contain from 0.5 to 15% by weight of the hydrogenation-active component, based on the catalyst.

In the case of impregnation methods, the degree of loading of the support can be varied over a wide range by varying the concentration of the metal salt solution and by repeating the impregnation procedure one or more times. Metal concentrations of 0.1 to 30% by weight, preferably 0.5 to 10 and more preferably 1 to 5% by weight, based on the catalyst, can be obtained.

The greatest flexibility in respect of setting the metal content in the catalyst is achieved by using precipitation methods, regardless of whether the metal component is applied to the previously made support or metal component and support component are precipitated jointly. In this procedure, the desired metal content can be determined freely by selection of the ratios of metal and support. Precipitated catalysts usually contain, depending on the metal selected, 0.1 to 30% by weight, preferably 0.5 to 10 and more preferably 1 to 5% by weight, of hydrogenation-active metal, based on the catalyst.

Pulverulent catalysts can, after being isolated, dried and calcined, be shaped together with a binder to form extrudates or pellets. Suitable binders are the various aluminum oxides, preferably boehmite, amorphous aluminosilicates having an $SiO_2/Al_2O_3$ weight ratio of 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$ and also clay. After shaping, the extrudates or compacts are again dried and, if desired, subsequently calcined.

Instead of providing the pulverulent catalysts with a binder, they can also be shaped directly after drying to form pellets or extrudates and can then be calcined. It has been found to be useful to add extrusion or peptization aids to the catalyst powder, for example methylcellulose, ethylcellulose, stearic acid, potato starch, formic acid, acetic acid, oxalic acid, alkali metal hydroxide solution, ammonia, amines or graphite.

The sizes of the extrudates and pellets depend on the individual requirements. The catalysts are usually used as 2–4 mm extrudates, as tablets having a diameter of 3 to 5 mm, as pellets having a size of 1.0 to 1.6 mm or in powder form, e.g. as fluidizable material having particle sizes between 50 and 400 μm.

The process of the invention can be carried out batchwise or continuously. The batchwise reaction procedure is carried out in autoclaves or pressure tubes. Continuous operation can be carried out in fixed-bed or moving-bed reactors. Fixed-bed reactors used are, for example, loop reactors, tray reactors, circulating gas reactors and preferably tube reactors. In the case of tube reactors, the ratio of reactor diameter to catalyst pellets is advantageously 2:1 to 20:1 and in particular 4:1 to 10:1.

In the following examples, there are described several preferred embodiments to illustrate the invention. However, it should be understood that the invention is not intended to be limited to the specific embodiments.

EXPERIMENTAL PROCEDURE

Examples 1 to 4 were carried out under isothermal conditions in a 75 ml stirring autoclave. 5,5-dimethyl-2-phenyl-1,3-dioxane was introduced into the reactor as a solution in dioxane after previous drying and 2 g of catalyst which had previously been heated at 300° C. for 30 minutes were added to the starting material. The apparatus was flushed with nitrogen and then charged with hydrogen until the reaction pressure had been reached.

For Examples 5 to 9, a stirring autoclave having a total volume of 350 ml was used. 200 ml of a solution of 5,5-dimethyl-2-phenyl-1,3-dioxane in cyclohexane (corresponding to 20 g of cyclic acetal) plus 1 g of pulverulent catalyst were employed.

For the continuous experiments (Examples 10 to 14), a coiled tube reactor having a length of 900 mm and an internal diameter of 6 mm was used. The reactor was charged with 2 g of catalyst which was dried for 30 minutes at reaction temperature in a stream of nitrogen (4.5 l/h) and was then reduced by passing a stream of hydrogen (10 l/h) over it for 12 hours at 250° to 400° C. The solution of the starting materials was then introduced into the reactor by a pump and the product stream was condensed in a cold trap at −30° C., warmed to room temperature and analyzed by gas chromatography.

The experiments 13 to 15 were carried out in a flow-through hydrogenation reactor having an internal diameter of 19 mm. 60 ml of a solution of 86.4 g/l of 5,5-dimethyl-2-phenyl-1,3-dioxane in cyclohexane were passed at 160° to 180° C. over 15 ml of catalyst which had previously been reduced for 3 hours at 200° C. with 15 l/h of hydrogen under atmospheric pressure. The product was analyzed as described above.

Catalyst Supports

1. H-[B]-silicate (H-[B]-ZSM5)

The borozeolite of the pentasil type was prepared by hydrothermal systhesis. For this purpose, 640 g of finely divided $SiO_2$, 122 g of $H_3BO_3$ and 8000 g of an aqueous 1,6-hexanediamine solution (amine:water=1:1 in parts by weight) were reacted at 170° C. under autogenous pressure in a stirred autoclave. The crystalline reaction product was filtered off, washed with water, dried for 24 hours at 100° C. and calcined for 24 hours at 500° C. The borozeolite comprised 94.2% by weight of $SiO_2$ and 2.3% by weight of $B_2O_3$. It was mixed with boehmite (60 parts by weight of zeolite, 40 parts by weight of boehmite) and shaped to form extrudates which were dried for 16 hours at 110° C. and calcined for 24 hours at 500° C. This support is denoted below by the letter A.

2. H-[Al]-ZSM5

The zeolite having an MFI structure which was used as support is a commercial product (product designation: SH-55) from Vereinigite Aluminum Werke VAW GmbH. The $SiO_2$/—$Al_2O_3$ molar ratio was 54:1. This support is denoted below by the letter B.

3. Silicalite

Silicalite was prepared by the following method:

A mixture of 200 g of an aqueous, 1M solution of tetra-(n-propyl) ammonium hydroxide and 200 g of water was added dropwise while stirring to 78.5 g of tetra ethyl orthosilicate. The mixture was stirred further for 1 hour and 300 g of ethanol were added. This mixture was stirred for a further 2 hours and then introduced into a 2.5 liter stainless steel autoclave. The hydrothermal synthesis was carried out with stirring (100 rpm) at 105° C. for a reaction time of 96 hours. The resulting crystals were separated off in a centrifuge, washed three times with water and then dried for 16 hours at 110° C. and calcined for 12 hours in air at 550° C. (heating rate: 1° C./min). This support is denoted below by the letter C.

4. $Al_2O_3$

The aluminum oxide used as support was manufactured by BASF and sold under the designation D10-10. It contained less than 0.1% by weight of each of Na, K and Fe. Its internal surface area was about 230 $m^2/g$, the pore volume (determined by water absorption) was about 0.7 $cm^3/g$ and the density was about 650 g/l. The aluminum oxide was stable up to 500° C. This support is denoted below by the letter D.

Catalyst Preparation

To prepare the catalysts, the support materials indicated in Table 2 were used. To apply the hydrogenation-active metal, a solution of $Cu(NO_3)_2.3H_2O$ or $Cu(CH_3COO)_2.H_2O$ was pumped over the support for 24 hours at 70° to 80° C. In place of the aqueous solution, it was also possible to use an ammoniacal solution of the copper salt. Loading with metal then occurred at a pH of 10.5. This procedure gave a higher copper concentration on the support in a shorter time than when using aqueous solutions. Instead of pumping the copper salt solution over the support material, it was also possible to stir copper salt solution and support in a flask at room temperature.

To load the support by ion exchange, it was stirred two or three times with the aqueous metal salt solution for 24 hours. The metal salt was used in a large excess. After ion exchange was complete, the catalyst was filtered off and washed, then dried and calcined.

Table 1 shows the catalysts used in the experiments. The type of support is, as described above, denoted by the letters A, B, C and D. A different copper content for the same support is indicated by figures after the letter.

TABLE 1

Catalysts

| Designation | Support | Cu concentration [% by weight based on catalyst] |
|---|---|---|
| A-1 | H-[B]-silicalite | 4.0 |
| A-2 | H-[B]-silicalite | 7.0 |
| B | H-[Al]-ZSM5 | 3.8 |
| C-1 | Silicalite | 5.9 |
| C-2 | Silicalite | 12.3 |
| D-1 | $Al_2O_3$ | 7.0 |
| D-2 | $Al_2O_3$ | 7.6 |
| D-3 | $Al_2O_3$ | 8.3 |

TABLE 2

Reduction of 5,5-dimethyl-2-phenyl-1,3-dioxane to 3-benzyloxy-2,2-dimethylpropanol

| Example | Reactor | Catalyst | Temp. [°C.] | Pressure [MPa] | Dioxane conversion [%] | Selectivity in respect of alcohol [%] | Remarks |
|---|---|---|---|---|---|---|---|
| 1 | Autoclave | C-1 | 190 | 9 | 5.0 | 42.0 | |
| 2 | Autoclave | C-2 | 190 | 9 | 50.0 | 75.0 | |
| 3 | Autoclave | A-1 | 190 | 9 | 70.0 | 90.0 | |

TABLE 2-continued

Reduction of 5,5-dimethyl-2-phenyl-1,3-dioxane to 3-benzyloxy-2,2-dimethylpropanol

| Example | Reactor | Catalyst | Temp. [°C.] | Pressure [MPa] | Dioxane conversion [%] | Selectivity in respect of alcohol [%] | Remarks |
|---|---|---|---|---|---|---|---|
| 4 | Autoclave | B | 190 | 9 | 98.0 | 85.0 | |
| 5 | Autoclave | A-3 | 195 | 9 | 89.4 | 97.0 | |
| 6 | Autoclave | A-3 | 195 | 9 | 69.4 | 82.0 | |
| 7 | Autoclave | D-1 | 195 | 9 | 64.8 | 82.2 | |
| 8 | Autoclave | D-3 | 195 | 9 | 80.6 | 87.5 | |
| 9 | Autoclave | D-3 | 205 | 9 | 93.6 | 92.0 | |
| 10 | Tube | C-2 | 190 | 9 | 50.0 | 92.0 | |
| 11 | Tube | A-2 | 300 | 0.1 | 74.0 | 44.1 | |
| 12 | Tube | A-2 | 190 | 0.1 | 40.0 | 74.0 | |
| 13 | Tube | D-2 | 180 | 3 | 98.1 | 59.7 | |
| 14 | Tube | D-2 | 160 | 3 | 91.3 | 76.7 | |
| 15 | Tube | D-2 | 170 | 3 | 99.2 | 64.6 | |

Various modifications of the process of the invention may be made without departing from the spirit or scope thereof and it should be understood that the invention is intended to be limited only as defined in the appended claims.

What we claim is:

1. A process for preparing 3-oxyalkyl-propan-1-ols of the formula

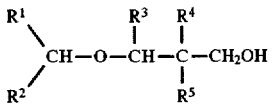

comprising hydrogenating 1,3-dioxanes of the formula

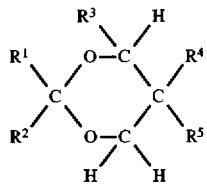

wherein $R^1$, $R^2$, $R^4$ and $R^5$ are individually selected from the group consisting of a) hydrogen, b) straight-chain or branched alkyl, alkenyl and alkynyl of up to 18 carbon atoms, c) cycloalkyl and cycloalkenyl of 5 to 8 carbon atoms, d) aryl, alkylaryl, aralkyl, aralkenyl and alkenylaryl of 6 to 16 carbon atoms and e) heterocyclics or $R^1$ and $R^2$ and/or $R^4$ and $R^5$ together with the carbon atom to which they are attached form a cycloalkane, cycloalkene or heterocycle of 5 to 7 ring atoms, $R^1$, $R^2$, $R^4$ and $R^5$ optionally substituted with an inert member under the reaction conditions, and $R^3$ is hydrogen or a straight-chain or branched alkyl, at pressures of from 0.1 to 35 MPa and temperatures of from 40° to 500° C. in the presence of catalysts, wherein the catalysts comprise at least one metal selected from the group consisting of group IB of the Periodic Table of the Elements, with the exception of chromium and nickel, as hydrogenation-active component and an acid support.

2. The process of claim 1, wherein the 1,3-dioxanes which are reacted are compounds of the formula

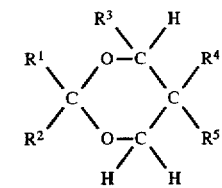

wherein $R^1$, $R^2$, $R^4$ and $R^5$ are individually selected from the group consisting of a) hydrogen, b) alkyl of 1 to 12 carbon atoms, alkenyl and alkynyl of 2 to 12 carbon atoms, c) cycloalkyl and cycloalkenyl of 5 or 6 carbon atoms, d) aryl, alkylaryl, aralkyl, aralkenyl and alkenylaryl of 6 to 12 carbon atoms, e) heterocyclic containing at least one ring member selected from the group consisting of nitrogen, oxygen and sulfur and $R^3$ is hydrogen or alkyl of 1 to 12 carbon atoms.

3. The process of claim 1, wherein the hydrogenation-active component is selected from the group consisting of molybdenum, tungsten, ruthenium, cobalt, rhodium, iridium, palladium, platinum and copper.

4. The process of claim 1, wherein the catalysts contain from 0.5 to 30% by weight of the hydrogenation-active component (based on the catalyst).

5. The process of claim 1, wherein the catalysts comprise zeolites as support.

6. The process of claim 5, wherein the support is zeolite of the pentasil type.

7. The process of claim 5, wherein the zeolite is selected from the group consisting of an aluminosilicate, borosilicate and iron silicate zeolite of the pentasil type.

8. The process of claim 5, wherein the zeolite is doped with at least one member selected from the group consisting of transition metals of groups VIB, VIIIB, IB and IIB of the Periodic Table, with the exception of chromium and nickel.

9. The process of claim 5, wherein the zeolite is doped with noble metals.

10. The process of claim 5, wherein the zeolite is doped with metals of the rare earths.

11. The process of claim 1, wherein the hydrogenation catalyst comprises phosphates as support.

12. The process of claim 11, wherein the phosphates are selected from the group consisting of aluminum phosphate, cerium phosphate, zirconium phosphate, boron phosphate, iron phosphate, strontium phosphate, silicon aluminum phosphate, silicon iron aluminum phosphate and are used individually and as mixtures of two or more phosphates.

13. The process of claim 11, wherein the phosphates are doped with metals selected from the group consisting of groups IA, IIA, IIIA, IVA and VA of the Periodic Table, with transition metals of groups IVB to VIIIB, IB and IIB, with the exception of chromium and nickel, with metals of the rare earths and with uranium.

14. The process of claim 1, wherein the hydrogenation catalyst comprises an acid or amphoteric metal oxide as support.

15. The process of claim 14, wherein the support is at least one member selected from the group consisting of an oxide of metals of groups IIIA, IVA or groups IVB to VIB of the Periodic Table, with the exception of chromium oxide, and mixtures of two or more such oxides.

16. The process of claim 5, wherein the zeolites, phosphates and/or metal oxides are treated with inorganic or organic acids.

17. The process of claim 1, wherein the reaction is carried out at pressures of from 3 to 15 MPa and at temperatures of from 100° to 450° C.

18. The process of claim 1, wherein the molar ratio of hydrogen to 1,3-dioxanes is from 0.2:1 to 250:1.

19. The process of claim 2, wherein $R^3$ is hydrogen.

20. The process of claim 18, wherein the molar ratio is 1:1 to 100:1.

* * * * *